United States Patent
Huynh et al.

(10) Patent No.: US 10,981,136 B2
(45) Date of Patent: *Apr. 20, 2021

(54) NATURAL WATER-INSOLUBLE ENCAPSULATION COMPOSITIONS AND PROCESSES FOR PREPARING SAME

(71) Applicant: Capol Inc., Saint-Hubert (CA)

(72) Inventors: Kim Uyên Huynh, Sainte-Julie (CA); François Cormier, Saint-Bruno (CA)

(73) Assignee: Capol Inc., Saint-Hubert (CA)

( * ) Notice: Subject to any disclaimer, the term of this patent is extended or adjusted under 35 U.S.C. 154(b) by 441 days.

This patent is subject to a terminal disclaimer.

(21) Appl. No.: 15/933,852

(22) Filed: Mar. 23, 2018

(65) Prior Publication Data

US 2018/0207603 A1 Jul. 26, 2018

Related U.S. Application Data

(63) Continuation of application No. 11/793,755, filed as application No. PCT/CA2005/001853 on Dec. 6, 2005, now abandoned.

(60) Provisional application No. 60/637,730, filed on Dec. 22, 2004.

(51) Int. Cl.
| | |
|---|---|
| A23P 10/30 | (2016.01) |
| B01J 13/04 | (2006.01) |
| A23L 27/00 | (2016.01) |
| A23L 5/43 | (2016.01) |
| A23L 5/44 | (2016.01) |
| A23L 5/47 | (2016.01) |
| A61K 8/14 | (2006.01) |
| A61K 8/64 | (2006.01) |
| A61Q 1/06 | (2006.01) |
| C08L 89/00 | (2006.01) |
| A61K 9/50 | (2006.01) |
| C09B 61/00 | (2006.01) |
| C09B 63/00 | (2006.01) |
| C09B 67/42 | (2006.01) |
| C09B 67/02 | (2006.01) |

(52) U.S. Cl.
CPC ............ *B01J 13/04* (2013.01); *A23L 5/43* (2016.08); *A23L 5/44* (2016.08); *A23L 5/47* (2016.08); *A23L 27/72* (2016.08); *A23P 10/30* (2016.08); *A61K 8/14* (2013.01); *A61K 8/64* (2013.01); *A61K 9/5052* (2013.01); *A61K 9/5089* (2013.01); *A61Q 1/06* (2013.01); *C08L 89/00* (2013.01); *C09B 61/00* (2013.01); *C09B 63/00* (2013.01); *C09B 67/0095* (2013.01); *C09B 67/0097* (2013.01); *A23V 2002/00* (2013.01)

(58) Field of Classification Search
None
See application file for complete search history.

(56) References Cited

U.S. PATENT DOCUMENTS

| | | |
|---|---|---|
| 833,602 A | 10/1906 | Immerheiser |
| 2,053,208 A | 9/1936 | Curtis |
| 3,461,128 A | 8/1969 | Colchester et al. |
| 3,885,052 A | 5/1975 | Starr |
| 3,909,284 A | 9/1975 | Woznicki et al. |
| 4,156,077 A | 5/1979 | Pifferi |
| 4,230,687 A | 10/1980 | Sair et al. |
| 4,232,047 A | 11/1980 | Sair et al. |
| 4,260,388 A | 4/1981 | Mirabel et al. |
| 4,274,830 A | 6/1981 | Woznicki et al. |
| 4,302,200 A | 11/1981 | Yokoyama et al. |
| 4,336,244 A | 6/1982 | Woznicki et al. |
| 4,475,919 A | 10/1984 | Woznicki et al. |
| 4,481,226 A | 11/1984 | Crosby et al. |
| 4,636,261 A | 1/1987 | Heinze |
| 4,683,256 A | 7/1987 | Porter et al. |
| 4,750,938 A | 6/1988 | Cottrell |
| 4,878,921 A | 11/1989 | Koga et al. |
| 4,999,205 A | 3/1991 | Todd, Jr. |
| 5,023,095 A | 6/1991 | Kirk |
| 5,079,016 A | 1/1992 | Tood, Jr. |
| 5,108,736 A | 4/1992 | Schlossman |
| 5,164,212 A | 11/1992 | Nafishi-Novaghar et al. |

(Continued)

FOREIGN PATENT DOCUMENTS

| | | |
|---|---|---|
| CA | \ 2591772 | 5/2013 |
| EP | 0328906 B1 | 10/1993 |

(Continued)

OTHER PUBLICATIONS

Amilina Native Starch Information Sheet, downloaded Jan. 7, 2015.

(Continued)

*Primary Examiner* — Ileana Popa

(74) *Attorney, Agent, or Firm* — Klarquist Sparkman, LLP

(57) ABSTRACT

The present invention relates to dry particulate encapsulation compositions comprising a water-insoluble matrix comprising at least 70% by weight of proteins, based on the total weight of the matrix and a moisture content of about 5 to 10% by weight, based on the total weight of the matrix and an encapsulate encapsulated in the matrix, wherein the matrix once wetted in a clear colorless aqueous solution or in mineral oil has a lightness value (L*) greater than about 40, a color vividness or Chroma (C*) lower than about 33 and a hue angle between about 70 and 90. The encapsulation compositions of the present invention are useful in encapsulating dyes, medications and vitamins. Fine particulate encapsulation compositions comprising natural dyes can be used in lieu of artificial lakes in confectionery, cosmetics and caplets color coatings.

24 Claims, No Drawings

(56) References Cited

U.S. PATENT DOCUMENTS

| | | | |
|---|---|---|---|
| 5,183,690 | A | 2/1993 | Carr et al. |
| 5,393,333 | A | 2/1995 | Trouve |
| 5,411,746 | A | 5/1995 | Signorino et al. |
| 5,418,010 | A | 5/1995 | Janda et al. |
| 5,460,823 | A | 10/1995 | Jensen et al. |
| 5,591,455 | A | 1/1997 | Signorino |
| 5,601,865 | A | 2/1997 | Fulger et al. |
| 5,603,971 | A | 2/1997 | Porzio et al. |
| 5,690,857 | A | 11/1997 | Osterried et al. |
| 5,756,136 | A | 5/1998 | Black et al. |
| 5,792,505 | A | 8/1998 | Fulger et al. |
| 5,897,897 | A | 4/1999 | Porzio et al. |
| 5,958,502 | A | 9/1999 | Fulger et al. |
| 6,037,000 | A | 3/2000 | Chang et al. |
| 6,132,791 | A | 10/2000 | Fox |
| 6,143,344 | A | 11/2000 | Jon et al. |
| 6,179,839 | B1 | 1/2001 | Weiss et al. |
| 6,187,351 | B1 | 2/2001 | Porzio et al. |
| 6,190,686 | B1 | 2/2001 | Isager et al. |
| 6,221,417 | B1 | 4/2001 | Sas et al. |
| 6,329,010 | B1 | 12/2001 | Marquinet |
| 6,358,547 | B1 | 3/2002 | Dupont |
| 6,416,799 | B1 | 7/2002 | Porzio et al. |
| 6,436,455 | B2 | 8/2002 | Zietlow et al. |
| 6,500,463 | B1 | 12/2002 | van Lengerich |
| 6,500,473 | B1 | 12/2002 | Koehler et al. |
| 6,511,536 | B1 | 1/2003 | Noguchi et al. |
| 6,639,113 | B2 | 10/2003 | Runge et al. |
| 6,652,895 | B2 | 11/2003 | Porzio et al. |
| 6,719,839 | B2 | 4/2004 | Isager et al. |
| 6,730,342 | B2 | 5/2004 | Saito et al. |
| 6,790,453 | B2 | 9/2004 | Porzio et al. |
| 9,687,807 | B2 | 6/2017 | Huynh et al. |
| 2002/0165285 | A1 | 11/2002 | Runge et al. |
| 2003/0091698 | A1 | 5/2003 | Marsland |
| 2008/0160084 | A1 | 7/2008 | Huynh et al. |
| 2011/0256199 | A1 | 10/2011 | Zasypkin |
| 2016/0375421 | A1 | 12/2016 | Huynh et al. |

FOREIGN PATENT DOCUMENTS

| | | | |
|---|---|---|---|
| EP | | 1072650 A1 | 1/2001 |
| EP | | 0750854 B1 | 10/2001 |
| EP | | 1180332 A1 | 2/2002 |
| EP | | 1219292 A1 | 7/2002 |
| EP | | 1452098 A1 | 9/2004 |
| GB | | 1073366 | 6/1967 |
| JP | | 52-013527 | 1/1977 |
| JP | | 63-188363 A | 8/1988 |
| JP | | 03-097761 A | 4/1991 |
| JP | | 07-099925 A | 4/1995 |
| JP | | 08-053369 A | 2/1996 |
| JP | | 08-509231 A | 10/1996 |
| JP | | 10330637 | 12/1998 |
| JP | | 2000-004828 A | 1/2000 |
| JP | | 2000-504216 | 4/2000 |
| JP | | 2002-000230 A | 1/2002 |
| JP | | 2002-262824 A | 9/2002 |
| JP | | † 5744955 B2 | 5/2015 |
| WO | WO 1991/006286 A1 | | 5/1991 |
| WO | WO 1994/023702 A1 | | 10/1994 |
| WO | WO 1996/028983 A1 | | 9/1996 |
| WO | WO 1997/026802 A1 | | 7/1997 |
| WO | WO 2000/070967 A1 | | 11/2000 |
| WO | † WO 2001/025414 A1 | | 4/2001 |
| WO | WO 2002/034238 A2 | | 5/2002 |
| WO | WO 2003/045167 A1 | | 6/2003 |
| WO | WO 2004/016288 A1 | | 2/2004 |
| WO | WO 2004/073423 A1 | | 9/2004 |

OTHER PUBLICATIONS

Arêas, "Extrusion of Food Proteins," *Crit Rev Food Sci Nutr.* 32:365-392, 1992.
Beck, "Powder Plating with Natural Colors," *The World of Food Ingredients*, p. 73, Jun. 2012.
Belitz et al., "Introduction: Chapter 1: Amino Acides, Peptides and Proteins; Chapter 4: Carbohydrates," *Food Chem.*, pp. 16-83, 261-270, and 315-325, Springer, 2009.
Berset, "Color," in *Extrusion Cooking, Mercier et al.* (eds.), Chapter 12, pp. 371-385, Am. Association of Cereal Chemists, St. Paul, MN, 1989.
Camire, "Functionality Modification by Extrusion Cooking," *JAOCS* 68:200-205, 1991.
Carr et al., "Encapsulation of Atrazine Within a Starch Matrix by Extrusion Processing," *Cereal Chem.* 68:262-266, 1991.
Doane et al., "Encapsulation of Pesticides Within a Starch Matrix," *ACS Symposium Series* 53:74-83, 1977.
Fellows, Food Processing Technology: Principles and Practice, Parts 1-4, Chapter 14, pp. 294-308, 2000.
Frame, N.D. (editor), "The Technology of Extrusion Cooking," Springer-Science+Business Media Dordrecht, 1994, preface.
Gorton, "Natural Selection," *Baking & Snack*, pp. 64-65, Mar. 2012.
Guy, "Chapter 2: Raw Materials for Extrusion Cooking Processes," in The Technology of Extrusion Cooking, Frame, N.E. (ed.), Springer-Science+Business Media Dordrecht, 1994.
Kearns et al., "Extrusion and Texturized Proteins," in *Proceedings of the World Congress on Vegetable Protein Utilization in Human Foods and Animal Feedstuffs*, T.H. Applewhite (ed.), Amer Oil Chemists Society, Jul. 1989.
Kinnison, "Extrusion Effects on Colors and Flavors," *Snack Food*, pp. 40-42, 1972.
Kuhnen & Wacker, letter re Oral Proceedings in EP 00 954 113.7, dated May 18, 2007.
Kumari, Extrusion Technology, Theory Study Material, Acharya N.G. Ranga Agricultural University, May 2013.
Ledward and Tester, "Molecular Transformations of Proteinaceous Foods During Extrusion Processing," *Trends Food Sci Technol.* 5:117-120, 1994.
Lukiw, "Alzheimer's Disease and Aluminum, Minerals and Metal," in *Neurotoxicology*, Chapter 12, pp. 113-125, CRC Press, Boca Raton, FL.
Maga and Kim, "Stability of Natural Colourants (Annatto, Beet, Paprika, Turmeric) During Extrusion Cooking," *Lebensmittel-Wissenchaft & Technologie* 23:427-432, 1990.
Matthey and Hanna, "Physical and Functional Properties of Twin-Screw Extruded Whey Protein Concentrate-Corn Starch Blends," Lebensm.-Wiss. u.-Technol. 30:359-366, 1997.
Mortazavian et al., "Principles and Methods of Microencapsulation of Probiotic Microorganisms," *Iran J Biotechnol.* 5:1-18, 2007.
Nesterenko et al., Vegetable Proteins in Microencapsulation: A Review of Recent Interventions and Their Effectiveness, *Industrial Crops and Products* 42:469-479, 2013.
Onwulata et al., "Functionality of Extrusion—Texturized Whey Proteins," *J. Dairy Sci.* 86:3775-3782, 2003.
Onwulata et al., "Extrusion Texturized Dairy Proteins: Processing and Application," *Adv Food Nutri Res.* 62:173-200, 2011. (Abstract).
Ortiz et al., "Rheological and Thermal Properties of Extruded Mixtures of Rice Starch and Isolated Soy Protein," *Starch/Starke* 60:577-587, 2008.
† Particle Sciences, Inc., "Hot Melt Extrusion," Technical Brief, 2011.
Porzio, "Flavor Encapsulation: A Convergence of Science and Art," *Food Technology* 58:40-47, 2004.
Pro-Fam® 974, Isolated Soy Protein 066-974 Data Sheet, Aug. 28, 2013.
Prudencio-Ferreira and Arêas, "Protein-Protein Interactions in the Extrusion of Soya at Various Temperatures and Moisture Contents," *J Food Sci.* 58:378-381, 1993.
Purwati, "Structuring High-Protein Foods," Theses, Wageningen University, defended in public on Monday Mar. 12, 2012.
Qi and Onwulata, "Physical Properties, Molecular Structures, and Protein Quality of Texturized Whey Protein Isolate: Effect of Extrusion Moisture Content," *J Dairy Sci.* 94:2231-2244, 2011.
Qi and Onwulata, "Physical Properties, Molecular Structures, and Protein Quality of Texturized Whey Protein Isolate: Effect of Extrusion Temperature," *J Agric Food Chem.* 59:4668-4675, 2011.

(56) References Cited

OTHER PUBLICATIONS

Scott-Thomas, "Colarome's Plant-Derived Colors Come to the States," *Food Navigator-USA.com*, Dec. 2009.
Steel et al., "13. Thermoplastic Extrusion in Food Processing," in Thermoplastic Elastomers, Prof. Adel El-Sonbati (ed.), ISBN: 978-953-51-0346-02, InTech, Available from http://www.intechopen.com/books/thermoplasticelastomers/thermoplastic-extrusion-in-food-processing, 2012.
Swarbrick, "Coarse Dispersions, Remington: the Science and Practice of Pharmacy," $20^{th}$ Edition, pp. 316-334, 2000.
Tolstoguzov, "Thermoplastic Extrusion—the Mechanism of the Formation of Extrudate Structure and Properties," *JAOCS* 70:417-420, 1993.
USDA Basic Report 20061 Rice Flour, downloaded Jan. 7, 2015.
USDA Basic Report 20466 Semolina, downloaded Jan. 7, 2015.
USDA Basic Report 48052 Vital Wheat Gluten, downloaded Jan. 7, 2015.
Van Lengerich, "Influence of Extrusion Processing on In-Line Rheological Behavior, Structure, and Function of Wheat Starch, Dough Rheology and Baked Product Texture," pp. 421-471, 1990.
Verbeek and van den Berg, "Extrusion Processing and Properties of Protein-Based Thermoplastics," *Macromol Mater Eng.* 294:10-21, 2010, first published online Nov. 4, 2009, DOI: 10.1002/mame.200900167.
Vingerhoedes and Harmsen, "Proteins: Versatile Materials for Encapsulation," Chapter 4: Microencapsulation Using Proteins, pp. 85-102, 2004.
Vitalis Nutrition Production Specification, downloaded Jan. 6, 2015.
Yilmaz et al., "Effect of Glycerol on the Morphology of Starch-Sunflower Oil Composites," *Carbohydr. Polymers* 38:33-39, 1999.
Yilmaz et al., "Encapsulation of Sunflower Oil in Starch Matrices via Extrusion," *Carbohydr. Polymers* 45:403-410, 2001.
Yilmaz et al., "Modulated Release of a Volatile Compound from Starch Matrixes Via Enzymatically Controlled Degradation," *Biomacromolecules* 3:305-311, 2002.
Yuryevd, et al., Structure of Protein Texturates Obtained by Thermoplastic Extrusion, *Die Nahrung* 34:607-613, 1990.
JP 2007-547117 Office Action dated Nov. 15, 2011 (dated Nov. 22, 2011), original and English versions.
† JP2013082858 Amended Claims filed Mar. 14, 2014 (Japanese).
† JP2013082858 Amended Claims filed Mar. 14, 2014 (English translation).
† JP2013082858 Petition filed Mar. 14, 2014 (Japanese).
† JP2013082858 Office Action dated May 13, 2014 (Japanese).
† JP2013082858 Office Action dated May 13, 2014 (English translation).
† JP2013082858 Amended Claims filed Sep. 12, 2014 (Japanese).
† JP2013082858 Amended Claims filed Sep. 12, 2014 (English translation).
† JP2013082858 Response filed Sep. 12, 2014 (Japanese).
† JP2013082858 Response filed Sep. 12, 2014 (English translation).
† JP2013082858 Agent Letter dated Sep. 22, 2014 (English).
† JP2013082858 Grant Decision dated Mar. 31, 2015 (Japanese) with Agent Letter dated Apr. 2, 2015 (English).
PCT/CA2005/001853 International Search Report dated Apr. 5, 2006.
PCT/CA2005/001853 Written Opinion dated Apr. 5, 2006.
PCT/CA2005/001853 International Preliminary Report on Patentability dated Jul. 5, 2007.
† U.S. Appl. No. 11/793,755 Patent Trial and Appeal Board Decision on Appeal dated Jan. 30, 2018 (19 pages).

NATURAL WATER-INSOLUBLE ENCAPSULATION COMPOSITIONS AND PROCESSES FOR PREPARING SAME

CROSS-REFERENCE TO RELATED APPLICATIONS

This application is a continuation of U.S. application Ser. No. 11/793,755, filed Jun. 21, 2007, now abandoned, which is the U.S. National Stage of PCT/CA2005/001853 filed Dec. 6, 2005, which claims priority to U.S. Provisional Application No. 60/637,730 filed on Dec. 22, 2004.

FIELD OF THE INVENTION

The present invention relates to encapsulation compositions and techniques in which an encapsulate is encapsulated in a natural water-insoluble matrix. More particularly, the present invention relates to the encapsulation of natural colorings, vitamins, food supplement and medicines. The present invention further relates to extrusion processes for preparing same.

BACKGROUND OF THE INVENTION

Dyes and lakes are used to provide attractive colors to foods, cosmetics and pharmaceuticals. Lakes are insoluble coloring matters. They can be dispersed in a solution to provide color and opalescence. Most lakes are made from a dye immobilized onto the surface of an aluminum substratum to form an insoluble complex (see for example U.S. Pat. Nos. 833,602, 2,053,208 and 3,909,284 which describe methods of producing artificial lakes).

Lakes are opaque and their color is seen by reflectance of light. They are used essentially anywhere insoluble pigments are appropriate, including in dry or oil-based products where there is insufficient moisture for water-soluble dyes, or products where migration of a soluble dye would be a problem. Typical applications include, but is not limited to, colored candy coating of panned candies, breakfast cereals, nuts, multilayered food stuff (e.g., cakes) cosmetics (e.g., blush and lipsticks) and pharmaceutical capsules, dragees, tablets and the like. Most lakes are made of chemically-synthesized artificial dyes. An exception to this is carmine, an aluminum lake of natural carminic acid extracted from the insect *Dactilopius coccus*.

Various means of producing water insoluble coloured material have been developed. One approach has been to immobilize dyes onto the surface of insoluble compounds. U.S. Pat. No. 4,475,919 describes a method to lake natural dyes onto the surface of natural insoluble polymers such as cellulose, microcrystalline cellulose, cellulose derivatives such as ethyl cellulose, starch or starch derivatives. Examples of natural dyes include anthocyanins, turmeric and annatto. An aluminum salt is used as a dyeing aid. In addition, JP Patent No. 10330637 teaches a method to immobilize natural lake dyes onto the surface of an aluminum substratum namely aluminum hydroxide. In both instances, the natural dyes are adsorbed onto a surface and are therefore not protected from detrimental physical or chemical factors. Furthermore, the use of aluminum as a substratum is of growing concern since it has been recognized for some time as a neurotoxic agent (Lukiw W J (1997) Alzheimer's Disease and Aluminum. In "Minerals and metal neurotoxicology" CRC Press, Boca Raton, Fla., pp. 113-125).

Yet another approach for producing water insoluble coloured material has been to develop a media for the dispersion of water insoluble dyes and lakes. U.S. Pat. No. 5,393,333 teaches a method of dispersing lakes in a mixture comprised of a film forming substance, a colouring and a plasticizer. The mixture is taught as useful in coloring the surface of medicinal tablets. PCT application No. 00150714US describes a method to disperse artificial lakes by use of a mixture of a hydrocolloid, namely gelatine and of a fatty acid. The fatty acid serves in maintaining viscosity of gelatine and in facilitating the dispersion of lakes.

Dispersion media have also been developed for natural water-insoluble dyes. European patent application No. 01219292/EP-A1 reports the use of a soy protein isolate to disperse carotenoids namely astaxanthin, canthaxanthin, lutein, zeaxanthin, citraxanthin and, ß-apo-8'-caroteneethyl-ester in an aqueous solution. The soy protein isolate was partially hydrolysed using enzymes to improve hydrocolloid properties. It has been demonstrated that carotenoids dispersed in such hydrocolloid are protected against oxidation by free radicals and retain their antioxidant activity. Similarly, International publication WO 03045167 describes methods to stabilize crystalline lycopene by reacting lycopene with a native soy protein isolate or an alkali-treated soy protein isolate. U.S. Pat. No. 6,719,839 describes a method to obtain a dispersed suspension of a natural dye in a hydrocolloid solution. Most examples of hydrocolloids are mixtures of gelatine and Arabic gum. The solubilisation of the mixture of dye and hydrocolloid is carried out at alkaline pH. Natural water-insoluble dyes include porphyrin, turmeric, vegetable black and annatto. The method can also be used with the natural lake, carmine.

Many of the above-mentioned water-insoluble dyes are known to bind to proteins. Thus aqueous solutions of water-soluble proteins can be used to maintain homogenized mixtures of protein and water-insoluble dyes dispersed. It can be expected that the shelf life of such preparations could be extended by the use of antimicrobial compounds. They might nevertheless have a limited shelf life due to the high water activity of the solutions and could not be used to colour oil-based products unless they were dried. Furthermore, because of limitations on the concentration of the protein in the aqueous solutions, it can be expected that a bulking agent such as maltodextrin would have to be added to the dispersed colour solution to carry out spray drying. The presence of maltodextrin in the spray-dried colour could provoke a fading of the colour when used in lipid-based products wherein maltodextrin would not dissolve.

Several other patents describe methods of rendering dyes insoluble by encapsulation into an insoluble matrix. U.S. Pat. No. 6,037,000 describes a method of producing small insoluble particles of encapsulated dye or lake. It involves dispersing the lake or dye into a melted matrix and forming small solid particles of the mixture by spray congealing. The only examples given are for the encapsulation of artificial lakes in a matrix comprised of polyethylene. As such, applications seem limited to toiletries and cosmetics because polyethylene is not suitable for foods. In addition, European Patent EP 0 750 854 describes a method to encapsulate dyes in an insoluble protein matrix. The method involves mixing the dye and a protein in water, adding a non-polar phase and homogenizing to obtain a water-in-oil dispersion and subjecting same to very high pressures between 15,000 and 200,000 psig to render the protein matrix insoluble. The coloured particles can then be separated from the non-polar phase and dried. This process involves the use of expensive pressurized equipments and can only be carried out batchwise.

U.S. Pat. No. 4,230,687 describes a method to encapsulate flavourings into a melt of encapsulating mixture comprised of 44% caseinate based on the weight of the encapsulate and of the encapsulating mixture. The resulting product which is described as sticky, viscous, plastic and non-flowable, is shaped into a sheet, dried and ground into a powder. As with other processes described above, solubilisation of the protein requires the use of an alkali that can be detrimental to alkali-sensitive active agents such as natural dyes of the group of anthocyanins. Furthermore, heating of the protein matrix generates Maillard reactions causing the formation of brown pigments that would alter the colour of an encapsulated dye.

Encapsulation of active agents can also be accomplished by extrusion. Extrusion is a continuous process that carries out several functions namely mixing and kneading liquid and solid ingredients, cooking them under a pressure that results in the formation of a melt and shaping ingredient by use of a dye. This process is accomplished over a relatively short period, typically between 1 to 2 minutes and heat may be applied over a much shorter period. Many extruded food products such as pasta, pet food, breakfast cereals and meat extenders have been coloured with artificial dyes. In most instances, extruded products are comprised of a substantial proportion of carbohydrates, e.g., starch of extruded flours, meals or grits, or syrup in extruded confectioneries, that limits the impermeability of extruded products to water. For example, Kinnison (1971; Effects of extrusion on food colors; Snack Food Color Service Lab., Warner-Jenkinson Co. 60(10): 50-51) reports the extrusion of corn grits and eight artificial dyes at temperatures that provoke product expansion. It was reported that the artificial dyes could sustain the high temperatures used in this type of process. U.S. Pat. No. 6,436,455 describes a process to manufacture marshmallows by extrusion of a mixture of gelatine, syrup and dye. It is likely that natural dyes would be destroyed in such high temperature processes. Furthermore, the high carbohydrate content and porous nature of the expanded products are expected to convey little protection against moisture.

There have been a few reports on the use of natural dyes in extruded products. Maga and Kim (1990; Stability of natural colorants [annatto, beet, paprika, turmeric] during extrusion cooking. Lebensmittel-Wissenchaft & Technologie, 23(5): 427-432) have studied the stability of natural dyes namely annatto (bixin and norbixin), beet red, paprika oleoresin and turmeric, in rice flour extruded at 125° and 155° C. The dyes were shown to be sensitive to heat, the most sensitive being beet red. Berset (1989; Color; Chapter 12. In: "Extrusion cooking". Mercier C et al., Eds, AACC, St. Paul, Minn., pp. 371-385) has performed a similar study on ß-carotene, canthaxanthin and annatto incorporated by extrusion in rice starch. Results also showed a sensitivity of the colourings to heat.

Extrusion can be carried out at temperatures low enough to enable the encapsulation of flavor compounds using a non-conventional extrusion setup. U.S. Pat. No. 5,756,136 describes a method to encapsulate cinnamaldehyde into a mixture of carbohydrates and whey using an extruder. Cinnamaldehyde which is the major component of cinnamon flavor, inhibits the leavening of dough by yeasts. It was demonstrated that the encapsulated cinnamaldehyde could be incorporated into dough without inhibiting yeast leavening. U.S. Pat. No. 6,790,453 describes the composition of a matrix used to encapsulate medications, pesticides, vitamins, preservatives and flavoring agents. The matrix comprises various mixtures of Arabic gum, polyols and gelatine. Matrices used in the encapsulation of flavor compounds possess polar characteristics that enable the release of flavor compounds so that they can be smelled and tasted in aqueous media.

There is growing concern over the safety of artificial dyes that are used in lakes. In fact, in recent years, the only colourings that have been withdrawn from the marketplace because of evidence of toxicity have been artificial. Furthermore, there is also concern about the use of aluminum since it has been recognized for some time as a neurotoxic agent and controversial etiopathogenic factor in several neurological disorders (Lukiw W J; 1997; Alzheimer's Disease and Aluminum. In "Minerals and metal neurotoxicology" CRC Press, Boca Raton, Fla., pp. 113-125). In addition, although Carmine (i.e., carminic acid extracted from an insect plated into an aluminum salt) is generally used as a natural lake, its animal origin is not deemed suitable for kosher, Hallal and vegetarian diets.

Thus, there remains a need for natural non-toxic colouring agents.

More particularly, there remains a need for natural lakes free of aluminum or other neurotoxic agents or suspected health hazardous agents for colouring foods, cosmetics, medicines and the like.

There also remains a need for bright, long lasting, unfading natural lake dyes.

Furthermore, there remains a need for an improved and inexpensive process to produce natural lake dyes which does not use natural dye damaging agents (e.g., alkali solutions) or extensive heating thereby causing a Maillard Reaction and altering the color of the natural dye.

In addition, there remains a need for an improved process which enables the encapsulation of labile active agents, such as natural dyes, which limits the release of the active agent in water.

There remains a need for natural lakes suitable for particular diets such as vegetarian, kosher and Hallal diets. The present invention seeks to meet these needs and other needs.

The present description refers to a number of documents, the content of which is herein incorporated by reference in their entirety.

SUMMARY OF THE INVENTION

The present invention relates to colouring agents, encapsulation compositions and processes for making such compositions and colouring agents which overcome at least one of the drawbacks of the prior art.

The present invention is based on the discovery that labile active agents such as natural dyes can be encapsulated into a protein-rich matrix that limits the release of the active agent in water. Indeed, It was found that melt extrusion can be performed on protein-rich mixtures of a protein concentrate, or a protein isolate, using for example natural dyes, by incorporating a high concentration of water under conditions which enable the formation of a melt, while limiting the formation of undesirable brown colors through Maillard reactions.

The process of the present invention also has the advantage of limiting the degradation of labile dyes or other encapsulated material (e.g., medicines, food supplements, vitamins etc). In one embodiment, the extruded product thus obtained is dried to a moisture content of between 5% and 10% and ground, yielding a dry particulate composition.

The teachings of the present invention are applicable to a wide number of active agents and natural dyes, as demonstrated by several examples carried out with vitamins and dyes belonging to various chemical groups.

The stabilization of labile dyes is performed simply by the extrusion process itself and may be further increased by coencapsulation with a stabilizing agent. The present invention also demonstrates that other compounds such as salts or acids, e.g., organic or inorganic acids, can be coextruded with natural dyes to alter the final hue.

The encapsulation composition and the process to perform the encapsulation of the present invention, give rise to novel products which can find application in foods, cosmetics and medications (e.g., tablets, capsules or granules). The novel products of the present invention could not be obtained through the technologies which were used and described prior to the present invention.

It is yet another benefit of the present invention that, since the matrix is comprised of a high concentration of protein, the release of the encapsulated active agent can occur in the presence of gastric proteases. Because of this, the protein matrix of the present invention is particularly useful in the encapsulation of medications, vitamins and food supplements and especially when time release of the composition after ingestion is sought. Of course, in view of the prevalence of diseases associated with sugar metabolism, the protein based compositions of the present invention find a significant advantage as opposed to the carbohydrate-based composition of the prior art.

Thus, the present invention relates to a composition of a dry powder comprised of an active agent encapsulated in a water-insoluble proteinaceous matrix. The active agent is a dye, a medicinal compound, vitamins, food supplements or other compounds. In one particular embodiment of the present invention, the active agent is a natural dye.

In one embodiment, the water-insoluble proteinacious matrix of the present invention is a soy protein isolate. In another embodiment, the proteinacious matrix is a rice protein concentrate which has the advantage of being hypoallergenic and more resistant to moisture (e.g., water), thereby being more efficient at retaining the encapsulate (e.g., certain dyes including beet red and turmeric). Other insoluble proteinacious matrices such as proteins from milk or whey, zein (from corn) or gluten (from wheat) may also be used in accordance with the present invention. Thus, any insoluble proteinacious matrices that are suitable for encapsulating an active agent such as a natural dye may be used in accordance with the present invention. In one particular embodiment, water-insoluble proteinacious matrices of plant origin are used. Of course, mixture of water-insoluble protein concentrates are also encompassed in the general description of the water-insoluble proteinacious matrix of the present invention.

The active agents that may be encapsulated by the methods of the present invention may be any active agent such as nutrients (e.g., vitamins, food supplements, etc.), pharmaceutical compositions (medications and mixture thereof, [e.g., tablets, granules or capsules]), pesticides (including insecticides, nematocides, herbicides, fungicides, microbicides, etc) or natural and artificial dyes. In the case of medications or pesticides, encapsulation may be carried-out in accordance with the present invention to achieve controlled release of the active agent. In the case of vitamins (and medicines), encapsulation may be used to protect the vitamin from air-oxidation thereby extending the shelf life of the vitamin. Natural dyes may be encapsulated and the resulting natural lakes of the present invention used to coat not only tablets, granules or capsules but also food such as panned candies, nuts, cakes and the like. The lakes may also be used in cosmetics such as in lipsticks, blush, eye shadow and the like. Of course the need for a controlled release is not limited to medications. Indeed, other encapsulates might benefit from a controlled release (e.g., vitamins).

In one embodiment, the active agent of the present invention is a dye, preferably, a natural dye. The encapsulated dyes of the present invention are particularly useful when it is desirable that the colouring does not migrate during the manufacturing (e.g., to one layer of product to another, in a cake for example), or within the finished product during storage and handling, or to avoid its coming off during handling.

The natural pigments or dyes of the present invention can be of any food grade or pharmaceutically acceptable water insoluble or soluble coloring matter derived from a natural source. In one particular embodiment of the present invention, the natural pigments or dyes of the present invention are derived from a plant material. Thus, the pigment may either be in a substantially pure form or it may be contained in the material in which it occurs naturally such as in a plant or animal material (e.g., semi-purified or crude extracts or homogenates). Optionally, the natural dyes of the present invention may be in combination with a food grade and/or pharmaceutically acceptable carrier.

Unlimiting examples of natural dyes or coloring agents that may be used in accordance with the present invention include, but are not limited to, carotenoids, porphyrins and flavonoids. Carotenoids which have yellow, orange or red colors occurs widely in nature and important sources are plants including grasses, the annatto tree, citrus species, *Capsicum annum, Crocus sativus* flowers and marigold flowers, marine algae, yeasts, several vegetables (e.g., tomatoes, carrots, peppers). Carotenoid can be divided into 3 classes: carotenoids hydrocarbons, xanthophylls and apocarotenoids. Non-limiting examples of carotenoids include, bixin, norbixin apocarotenals, canthaxanthin, capsanthin, capsorubin, saffron, β-carotene, crocin, occurring in paprika oleoresin astaxanthin (e.g., salmon), lutein (e.g., green beans, egg yolk), zeaxanthin (e.g., corn), citranaxanthin, *capsicum*, canthaxanthin, lycopene, violaxanthine, rhodoxanthin and derivatives thereof. Of course, other carotenoids exist, are known in the art and may be used in accordance with the present invention.

Further hydrophobic pigments which are useful in accordance with the present invention are curcuminoids, of which curcumin is the major pigment in turmeric, the colored oleoresin extract of the Curcuma root, porphyrin pigments such as chlorophylls, and vegetable carbon black, which is produced by fully carbonizing vegetable material and grinding it into a fine powder. In addition, pigments of the flavonoid family including flavones and flavonols, which are yellow, and the anthocyanins (e.g., from red cabbage, sweet potato, red radish, elderberry, grape and the like), which may be red, blue, or purple, depending on pH, may also be used in accordance with the present invention. Other non-limiting examples of natural dyes that may be used in accordance with the present invention include geniposide, sandalwood and sepia. Thus, any natural dye or coloring agent may be used in accordance with the present invention as long as it is non-toxic. Preferably, the coloring agents used in accordance with the present invention are suitable for human consumption. Preferably, coloring agents from plant origin (flowers, trees, cereals, vegetables, fruits etc), algae or microorganisms are used. While the present invention finds a preferred utility when directed at human consumption, it should not be so limited. Compositions of the present invention also finds utility in a variety of bioagro uses such as for example animal-directed consumption. Thus, although human consumption is preferred, animal consumption is also encompassed by the present invention.

Thus, in one embodiment, the present invention relates to natural lake dyes, which are encapsulated in a water-insoluble proteinacious matrix such as soy isolates or rice concentrates. In another embodiment, the proteinacious matrix is made of a mixture of protein concentrates/isolates. In one embodiment the lakes of the present invention are useful for coloring foodstuff such as coating candies and nuts. In another embodiment, encapsulated natural lake dyes of the present invention may be used in the cosmetic field such as in the composition of lipstick, blush, eye shadows and the like. In yet another embodiment, the natural lake dyes of the present invention are of pharmaceutical grade and may be used for color coating of tablets, capsules, granules and the like.

In yet a further embodiment, natural lake dyes of the present invention are of plant origin suitable for kosher, Hallal and vegetarian diets.

Another feature of the encapsulate of the present invention (e.g., natural lake dyes) is that they are non-toxic and free of aluminum or other neurotoxic agents.

A further feature of the present invention is that the color of the extrudate is homogenous because of the formation of a melt during extrusion. The combination of thorough mixing, high sheering and pressure raises the temperature and leads to the formation of a homogenous melt.

In one embodiment, additives are added prior to extrusion of natural dyes in order to alter the color characteristics. One non-limiting example includes extrudates made with red cabbage anthocyanins. Naturally, red cabbage anthocyanins extrudates are blue. The incorporation of tannic acid changes the color to mauve while the incorporation of calcium chloride provides a purple coloring preparation.

In another embodiment, several natural dyes from crude, semi purified or substantially purified origin may be mixed in different proportions in accordance with the present invention in order to produce a wide array of color that could not be achieved using a single dye. Color shades close to the three primary colors (yellow, red and blue) can be achieved as follows. For example, a blue color is obtained from red cabbage coloring, a red color, from a mixture of beet red, ascorbic acid and turmeric, bixin or norbixin and a yellow color, from crocin or from turmeric with bixin or norbixin. Any combination of natural dyes from crude, semi purified or substantially purified origin may be mixed in different proportions in accordance with the present invention to achieve a desired used.

In addition, colors may be lightened by dilution with an insoluble white powder such as titanium dioxide, calcium phosphate, microcrystalline cellulose or other material well known in the art. Of course the chosen lightening agent will be selected so as not to significantly affect one or more of the advantages which are provided by the compositions of the present invention (e.g., edibility, possible encapsulation of water soluble and water insoluble dyes, use in medicine coating for time release, etc).

Another characteristic of the extrudate of the present invention is that it is very brittle and can easily be milled to a fine powder, comprising natural pigments, in the form of bodies having an average size of less than 150 µm, less than 50 µm, less than 20 µm and even less than 10 µm. Compositions comprising small particles having an average size of less than 20 µm provide a homogenous coloration while compositions comprising particles having an average size larger than 150 µm provide glitter.

In a related embodiment, the encapsulates, e.g., dyes, vitamins food supplements, medicines and combinations thereof, of the present invention have improved stability against light, heating and oxygen related changes (e.g., efficiency of the medicines or the colour hue of a particular pigment).

In a further embodiment, the stability of the encapsulate of the present invention may further be increased by incorporating preservative agents or stabilizers prior to extrusion. Non-limiting examples of stabilizers and preservative agents that may be used in accordance with the present invention include α-tocopherol, ascorbic acid, benzoic acid, isoascorbic acid, butylated hydroxyanisole, butylated hydroxytoluene, sodium citrate, sorbic acid potassium or sodium bisulphite.

In one particular aspect, the encapsulated dyes of the present invention comprise a high dye concentration to produce thinner color coats with high color intensities. By allowing a lower application dosage relative to the actual amount of dye while producing brighter color, the encapsulated dyes of the present invention can permit significant manufacturing savings.

In order to provide a clear and consistent understanding of terms used in the specification and claims, including the scope to be given such terms, a number of definitions are provided herein below.

Definitions

The use of the word "a" or "an" when used in conjunction with the term "comprising" in the claims and/or the specification may mean "one" but it is also consistent with the meaning of "one or more", "at least one", and "one or more than one".

Throughout this application, the term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the term "purified" refers to a molecule (e.g., pigment such as carotenoids, flavonoids, porphyrins) having been separated from a component of the composition in which it was originally present. Thus, for example, the carotenoid bixin has been purified to a level not found in nature. A "substantially pure" molecule is a molecule that is lacking in most other components (e.g., 30, 40, 50, 60, 70, 75, 80, 85, 90, 95, 96, 97, 98, 99, 100% free of contaminants). By opposition, the term "crude" means molecules (e.g., pigment) that have not been separated from the components of the original composition in which they were present. Therefore, the terms "separating" or "purifying" refer to methods by which one or more components of the sample are removed from one or more other components of the sample. Sample components include extracts from vegetables, fruits, flowers, cereals, insects or animals (including fish, crustaceans etc). The extracts may include all or parts of the components originally found in the natural source. Thus, apart from the pigment, the extract may include other components, such as proteins, carbohydrates, lipids or nucleic acids. In an embodiment, a separating or purifying step preferably removes at least about 50% (e.g., 50, 55, 60, 65, 70, 75, 80, 85, 90, 95, 96, 97, 98, 99, 100%) of contaminants. In another embodiment, a separating or purifying step removes at least about 80% (e.g., 80, 81, 82, 83, 84, 85, 86, 87, 88, 89, 90, 91, 92, 93, 94, 95, 96, 97, 98, 99, 100%) and, more preferably, at least about 95% (e.g., 95, 96, 97, 98, 99, 100%) of the other components present in the sample from the desired component. For the sake of brevity, the units (e.g., 66, 67 . . . 81, 82, . . . 91, 92% . . . ) have not systematically been recited but are considered, nevertheless, within the scope of the present invention.

As used herein, the term "extract" refers to a concentrated preparation of plant or animal origin including but not limited to vegetables, fruits, cereals, plants, flowers, trees, insects, crustaceans, yeasts or bacteria obtained by concentrating the active constituents (e.g., pigment) for example by evaporation of all or nearly all of the solvent and/or by removing undesired constituents in the sample.

The term encapsulate as used herein include dyes (e.g., pigment) of natural (e.g., carotenoids, flavonoids, porphyrins) and artificial origin (e.g., FD&C and D&C dyes) as well as other encapsulated material such as medicines (tablets, capsules, gels etc.), nutrients (food supplement, vitamins) pesticides or any other material that may be encapsulated by the methods of the present invention. An encapsulate of the present invention is an active agent which is combined with a protein matrix and extruded by a method disclosed herein.

The terminology "nature-identical dyes" as used herein refers to dyes which are identical to dyes extracted from natural sources but which are synthesized. Examples of commonly used natural-identical dyes include, but are not limited to, apocarotenal, β-carotene, apocarotenal ester, and canthaxanthin. As used herein, the terminology "natural pigment" or "natural dye" is used exclusively to designate pigments/dyes which are derived from a natural source.

The lightness value (L*). The lightness value is one of the three dimensions describing color (i.e., lightness (L*), hue (h) and chroma (C*)), well known in the art, of the CIELCh color space developed by the Commission Internationale d'Éclairage. It can be defined as the perceptual attribute that corresponds to how bright a color is relative to a white or highly transmitting reference (i.e., if a color appears to emit or reflect more or less light). Lightness also refers to the perception by which white objects are distinguished from gray objects, and light from dark colored objects. The value of lightness (L*) varies from 0 to 100 where 0 is black and 100 is white.

The hue value (h). In the CIELCh color space, hue is represented as an angle from 0° to 360°. Angles that range from 0° to 90° are reds, oranges and yellows. Those ranging from 90° to 180° are yellows, yellow-greens, and greens. Those ranging from 180° to 270° are green cyans (blue greens) and blues. Finally, those ranging from 270° to 360° are blues, purples, magentas, and return again to reds. An h value of 360° is reported as 0°.

The chroma value (C*). The chroma value is another color attribute and is used to specify the degree of saturation of color i.e., position of the color between grey and the pure hue for a same lightness.

The terminology "protein rich" used herein refers to a protein content of at least more than 69% protein by weight (70, 71, 72, 73, 74, 75, 76, 77, 78, 79, 80, 81, 82, 83, 84, 85, 86, 87, 88, 89, 90, 91, 92, 93, 94, 95, 97, 98, 99, 100%), preferably at least 75% and even more preferably at least 80%. Non-limiting examples of proteins that can be used as a matrix in accordance with the present invention include proteins from milk or whey, wheat (gluten), soy, mays (zein), rice or any mixtures thereof.

Other objects, features and advantages of the present invention will become apparent from the following illustrative description. It should be understood, however, that the illustrative description and the specific examples, while indicating specific embodiments of the invention, are given by way of illustration only, since various changes and modifications within the spirit and scope of the invention will become apparent to those skilled in the art from this description.

DESCRIPTION OF ILLUSTRATIVE EMBODIMENTS

It is thus an object of the present invention to provide a composition and a process to encapsulate a wide range of active agents including but not limited to dyes, vitamins and medicinal compounds inside a water-insoluble matrix in a particulate form. In one particular embodiment, the resulting particulate composition which contains natural dyes can be used in lieu of artificial lakes in confectionery, cosmetics and caplets color coatings where a natural coloring composition is preferred.

The encapsulation compositions of the present invention have improved shelf life and are useful in the preparation of products such as foods, cosmetics and medications. The present invention further relates to dry edible, natural color pigments that at the present time do not require certification by regulatory agencies since they utilize natural ingredients. The natural dye pigments of the present invention can be used as substitutes for artificial FD&C and D&C lakes that are commonly used for coloring food, drugs and cosmetics.

The process used to make the particulate composition is based on the use of melt extrusion under conditions that limit the formation of undesirable Maillard reaction's brown pigments and thus decrease the alteration of the color of the natural dyes. The present invention is particularly useful in the encapsulation of labile natural dyes. The process can be applied to either water-soluble dyes or water-insoluble dyes. Non-limiting examples of natural dyes that can be encapsulated by the methods of the present invention are presented in Table 1.

TABLE 1

Natural and nature-identical dyes used in foods, cosmetics and medicine color coating

| Group | Names of coloring | Source |
|---|---|---|
| anthraquinones | cochineal (carminic acid, carmine) | *Dactylopus coccus* |
| betalains | beet red (betacyanins, betaxanthins) | Beetroot (*Beta vulgaris*) |
| caramel | caramel | sugar and reactants |
| carotenoids | annatto (bixin, norbixin) | seeds of *Bixa orellana* |
| | apocarotenal | nature identical |
| | apocarotenal ester | nature identical |
| | canthaxanthin | nature identical |
| | β-carotene | *Blakeslea trispora* (natural) |
| | β-carotene | nature identical |
| | lycopene | tomato fruit |
| | lutein | alfalfa, marigold petals |
| | paprika (capsanthin, | fruits of *Capsicum* |

TABLE 1-continued

Natural and nature-identical dyes used in foods, cosmetics and medicine color coating

| Group | Names of coloring | Source |
| --- | --- | --- |
| | capsorubin) | *annuum* |
| | saffron (crocin) | stigmas of *Crocus sativus* |
| cucurminoids | turmeric (curcumin) | rhizome of *Curcuma longa* |
| flavins | riboflavin | |
| flavonoids | anthocyanins | various fruits and vegetables |
| porphyrins | chlorophyll and chlorophyllin | spinach, other |
| other | vegetable black | plant material |

The present invention is not limited to the encapsulation of natural dyes. Artificial dyes may also be used in accordance with the present invention. Non-limiting examples of artificial dyes that may be used include Allura Red, Amaranth, Erythrosine, Indigotine, Sunset Yellow, Brilliant Blue FCF, Fast Green FCF and Tartrazine. Artificial dyes encapsulated in the encapsulation compositions of the present invention become totally water-insoluble and do not migrate making them useful in a variety of applications such as in cosmetic compositions since they do not stain the skin. Of course, the skilled artisan to which the present invention pertains, when choosing an artificial dye, will choose same according to the use, desired utility and characteristics which are to be satisfied. Of course, mixtures of natural and artificial dyes (or mixtures of other encapsulates) are encompassed by the present invention. Similarly, mixtures of natural and nature identical dyes as well as mixtures of natural, nature identical and artificial dyes are encompassed by the present invention.

The encapsulation matrix in which an active agent of the present invention is encapsulated, comprises at least more than 69% protein by weight (70, 71, 72, 73, 74, 75, 76, 77, 78, 79, 80, 81, 82, 83, 84, 85, 86, 87, 88, 89, 90, 91, 92, 93, 94, 95, 97, 98, 99, 100%), more preferably at least 75% and even more preferably at least 80%. The process of the present invention can make use of both water-soluble and water-insoluble protein with minor adjustments to the process, e.g., assembly of extruder elements, operation parameters, ratio of liquids to solids, etc. The manufacturing process yields a water-insoluble matrix from water-soluble protein. Non-limiting examples of proteins that can be used in accordance with the present invention include proteins from milk or whey, wheat (gluten), soy, mays (zein), rice or mixtures thereof. Examples of mixture of proteins that may be used include 50:50, 25:75, 75:25, 90:10, 10:90, 40:60, 60:40 soy:rice or any other combination thereof. Mixtures of more than 2 proteins (e.g., 3, 4, 5 or more) may also be used in accordance with the present invention. For example, one non-limiting advantage of using a mixture of soy and rice proteins as a matrix would be to change the properties of the matrix as to render it more or less impermeable to water. By increasing the proportion of rice extracts relatively to soy proteins, the matrix becomes more resistant to moisture and thus retains the encapsulated material (e.g., dye, medicine, vitamin, food supplement, etc) better.

Consequently, by altering the composition of the matrix and by taking advantage of the different properties of proteins, one skilled in the art can easily adjust the impermeability of the encapsulated material. In addition, different proteins are digested at different rates in the gastro-intestinal tract. The time at which a medicine is released in the body may thus be adjusted by changing the composition of the matrix used to encapsulate it as well as the number of coating layers applied to the active ingredient. Thus, by changing the matrix composition or by increasing the number of layers (or thickness) of the encapsulation composition of the present invention, one can easily control the time and location (e.g., intestine vs stomach) at which the active ingredient is released. Of course the compositions can be adapted to take into account the particular animal to which the composition is administered.

Various additives can be added to the encapsulation matrix in accordance with the present invention namely, acids (e.g., organic or inorganic acids), salts, a calcium salt, e.g., calcium chloride, vitamins, to improve retention or the stability of the active agent or to modify the hue of an encapsulated dye. Other examples of stabilizers or preservative agents include α-tocopherol, ascorbic acid, benzoic acid, isoascorbic acid, butylated hydroxyanisole, butylated hydroxytoluene, sodium citrate, sorbic acid, or potassium or sodium bisulphate.

Optionally, the dry particulate composition can be enrobed inside a non-polar coating to provide a barrier to water. Non-limiting examples of non-polar coating that may be used include mixtures of waxes, oils, fats, long chain fatty acids, emulsifiers of natural origin (e.g., acacia, gelatin, lecithin, cholesterol) or of synthetic origin (e.g., sulfates or sulfonates), gums or zein. Additional non-limiting examples of emulsifying agents and other non-polar coatings that may be used in accordance with the present invention may be found in Remington (2000), The Science and Practice of Pharmacy, $20^{th}$ edition, pp: 318-334; and Rowe et al., Handbook of Pharmaceutical Excipients, 2003, 4th edition, Pharmaceutical Press, London UK.

Generally, the dyes/pigments or other encapsulated material of the present invention are obtained by extrusion of: 1) a protein extract (e.g., soy, rice, gluten, whey etc, or mixture thereof) which serves as a matrix; 2) an active agent or encapsulate (e.g., natural pigment either dissolved in a liquid or in a powdered form which can be directly mixed with the protein extracts, medicine etc.); 3) water; and 4) optionally, various stabilizers, preservative agents and, in the case of a pigment, various substances that serve to adjust the hue of the coloring agent (e.g., $CaCl_2$, acids, salts, etc). During this process, all ingredients are mixed together to form a homogenous paste. The extrusion is performed at low temperature and high moisture (approximately 30-50%) which reduce degradation of pigment and the alteration of its color by the Maillard reaction. The extrudate is then dried to a final moisture content of 5 to 10%. When dried, the extrudate is very brittle and can easily be milled to a fine powder of desired size. Particle size of less than 20 µm may be obtained with the extrudate of the present invention.

Thus, the process of the present invention is based on melt extrusion of a protein matrix combined with an extrudate such as dyes/pigments, medicines, vitamins or food supplements. While the precise apparatus to be used in achieving melt extrusion is not critical it has been found that a Baker-Perkin co-rotating twin-screw extruder (model MPF-50) is efficacious.

In one embodiment, elements of the extruder e.g., conveying screw, single-lead screw and kneading blocks, are aligned as to provide mixing, kneading and pressure buildup. The size of orifices at the exit also contributes to pressure buildup inside the extruder. Speed of rotation, alignment of elements of the extruder, i.e., kneading blocks and single-lead screws, and moisture content of the extrudate are determining factors of the amount of heat that is generated through shear force. Overheating of the mixture of protein, coloring and additive is prevented by circulation of chilled water in the extruder outer casing.

In another embodiment, where the encapsulation matrix comprises rice protein concentrate, the amount of moisture that may be used during the extrusion process ranges from about 30% to 50% (30, 31, 32, 33, 34, 35, 36, 37, 38, 39, 40, 41, 42, 43, 44, 45, 46, 47, 48, 49 and 50%) more particularly about 38% by weight, based on the total weight of the rice protein concentrate and water. In another embodiment, where the encapsulation matrix comprises soy protein isolate, the amount of moisture that may be used during the extrusion process ranges from about 45% to 70% (45, 50, 55, 60, 65 and 70%), more particularly about 55% by weight, based on the total weight of soy protein isolate and water. At moisture contents above the upper limit, the heat generated by shearing is not sufficient to enable proper protein texturization. At moisture contents under the lower limit, shear-induced heat is such that undesirable browning and coloring degradation occur.

In a particular embodiment, the selection of a suitable amount of a natural dye to be added to the protein matrix depends on the particular type of dye, the particular hue desired and the particular intended application. In a further embodiment, the encapsulated material contains an amount of coloring between 10 and 16,000 color units by weight (determined at the respective maximal absorbency wavelength of the colorings). In another embodiment, the encapsulated material contains an amount of coloring between 10 and 200 color units. In addition, several pigments may be added together in order to achieve a wide array of color that could not be achieved using a single dye. The selection of a suitable amount of the natural dye for the encapsulation process of the present invention depends on the particular type of pigment, on the particular intended application and on the desired appearance of the finished product. The relative amount of each dye depends on the particular color to achieve and thus any combination of dyes may be used in accordance with the present invention to suit particular needs. The achievement of particular colours by the mixture of colours is well known in the art.

In an embodiment, natural coloring preparations of very diverse color hues are obtained by varying the composition of dyes and additives. In a particular embodiment, fine powders of encapsulated natural dyes are dispersed in a media used in candy panning operations and dried to form opaque colored layers and are thus useful in candy coating, dragees coating or the like. Dragees or candy coating constitute a particular type of edible multilayered product where one or more coating layers, typically consisting of sugar, are applied onto a center of an edible ingredient. Non-limiting examples of such centers to be coated include, chewing gum, sugar tablets/granulates and chocolate. Coloring of such edible center is typically carried out in one or more panning steps where the centers are coated with sugar syrup containing the coloring agent. It is normally necessary to apply several coating layers to obtain a sufficient covering with color.

In one particular embodiment, the color intensity of the coloring compositions of the present invention (e.g., natural lakes) is proportional to the concentration of the encapsulated dye. Thus, It has been demonstrated that the amount of pigment required for coloring surfaces with the same color intensity is proportional to the concentration of the encapsulated dye present in the compositions of the present invention. It was discovered that the natural pigments of the composition of the present invention can comprise a high concentration of dye/natural pigment to produce thinner color coats with high color intensities. By allowing a lower application dosage relative to the actual amount of dye while producing brighter color, the encapsulated dyes of the present invention permit significant manufacturing savings. In other embodiments of the invention, the colorings were retained inside the encapsulation matrix to become non-staining. The encapsulated colorings could thus be used in applications where staining is a problem, such as in the field of cosmetics. In still another embodiment, powders of encapsulated colorings that leached coloring when in contact with water, are made impermeable by coating with a non-polar phase. Such compositions could also be used in applications where staining is a problem. In a further embodiment of the present invention, labile natural dyes become more stable once they are encapsulated.

In one particular embodiment, the dry particulate encapsulation composition of the present invention comprises (a) an encapsulate, encapsulated in a water-insoluble matrix comprising at least 70% by weight of protein, based on the total weight of the matrix, and a moisture content of about 5 to 10% by weight, based on the total weight of the matrix. In a particular embodiment, the matrix, once wetted in a clear colorless aqueous solution or in mineral oil has a lightness value ($L^*$) greater than 40, a color vividness or Chroma ($C^*$) lower than 33 and a hue angle between 70° and 90°.

In a further embodiment, the composition of the present invention is prepared by a process comprising:

(i) mixing an encapsulate (A), a matrix (B) and water in an extruder, to obtain a melted mixture which comprises encapsulate (A), matrix (B) and water;

(ii) extruding the melted mixture, to obtain an extruded mixture;

(iii) cutting the extruded mixture in small pieces (e.g., smaller than 10 mm, 8 mm, 6 mm, 5 mm, 4 mm);

(iv) drying the pieces of extruded mixture to a moisture content between 5 and 10% by weight, based on the total weight of dried extruded mixture; and (v) grinding the dried extruded mixture.

In an embodiment, the protein matrix retains completely or partially the encapsulate when the encapsulation composition of the present invention is dispersed into an aqueous solution.

The present invention is further illustrated by the following non-limiting examples.

Example 1

Colour Characteristics of an Extruded Soy Protein Isolate

A soy protein isolate was extruded without an encapsulate under conditions which enable the formation of a melt while minimizing undesirable Maillard reactions (see Table 3). The main impact on the color of the protein matrix was on lightness ($L^*$ value). The difference in the lightness of the dry powder prior to (Table 2) and after extrusion, i.e., $\Delta L^* = -10.2$, indicates a darkening of the soy protein isolate. Darkening was more apparent when the powder was immersed in a syrup or in oil, i.e., $\Delta L^* = -30.9$ and $-25$, respectively. Nevertheless, as seen in examples 2 through 8, the matrix of extruded soy protein isolate is adequate for the encapsulation of dyes while enabling the expression of colors.

TABLE 2

Color characteristics of the soy protein isolate and of the rice protein concentrate

| | Sample preparation prior to colorimeter readings | Colorimeter readings | | |
|---|---|---|---|---|
| | | L* | C* | H |
| soy protein isolate | none | 89.0 | 14.1 | 87° |
| | immersed in syrup | 73.8 | 22.4 | 81° |
| | immersed in oil | 69.8 | 25.6 | 81° |
| rice protein concentrate | none | 83.2 | 20.1 | 87° |
| | immersed in syrup | 58.5 | 30.6 | 81° |
| | immersed in oil | 55.9 | 29.1 | 80° |

TABLE 3

Examples of natural colorings and vitamin encapsulated in soy protein isolate by extrusion

| Extruder feed composition | | Sample preparation prior to colorimeter readings | Colorimeter readings | | |
|---|---|---|---|---|---|
| Ingredient | (g/min) | | L* | C* | H |
| Example 1: | | | | | |
| soy protein isolate | 240 | none | 78.8 | 20.2 | 84° |
| water | 300 | immersed in syrup | 42.9 | 24.0 | 76° |
| | | immersed in oil | 44.8 | 26.1 | 76° |
| Example 2: | | | | | |
| soy protein isolate | 240 | none | 51.5 | 10.4 | 254° |
| red cabbage color | 24 | immersed in syrup | 4.9 | 8.0 | 263° |
| water | 276 | immersed in oil | 5.7 | 6.0 | 267° |
| Example 3: | | | | | |
| soy protein isolate | 240 | none | 34.1 | 14.0 | 274° |
| red cabbage color | 24 | | | | |
| calcium chloride | 24 | immersed in syrup | 1.0 | 3.4 | 283° |
| water | 252 | immersed in oil | 2.1 | 3.8 | 274° |
| Example 4: | | | | | |
| soy protein isolate | 240 | none | 41.5 | 9.3 | 328° |
| red cabbage color | 24 | | | | |
| tannic acid | 2.4 | immersed in syrup | 5.4 | 7.7 | 299° |
| water | 273.6 | immersed in oil | 4.7 | 4.7 | 315° |
| Example 5: | | | | | |
| soy protein isolate | 240 | none | 43.1 | 28.4 | 9° |
| beet red | 24 | | | | |
| ascorbic acid | 6 | immersed in syrup | 5.1 | 14.9 | 10° |
| water | 270 | immersed in oil | 7.2 | 20.3 | 15° |
| Example 6: | | | | | |
| soy protein isolate | 240 | none | 41.2 | 28.3 | 23° |
| beet red | 24 | | | | |
| turmeric | 1 | | | | |
| ascorbic acid | 6 | immersed in syrup | 4.7 | 11 | 21° |
| water | 269 | immersed in oil | 5.4 | 14.3 | 21° |
| Example 7: | | | | | |
| soy protein isolate | 240 | none | 73.2 | 44.1 | 66° |
| norbixine | 0.48 | immersed in syrup | 31.8 | 53.5 | 63° |
| water | 299.5 | immersed in oil | 39.2 | 62.3 | 62° |
| Example 8: | | | | | |
| soy protein isolate | 240 | none | 71.8 | 54.6 | 83° |
| saffron | 2.4 | immersed in syrup | 41.5 | 56.7 | 78° |
| water | 297.6 | immersed in oil | 33.0 | 50.4 | 73° |
| Example 9: | | | | | |
| soy protein isolate | 240 | none | 75.1 | 65.0 | 88° |
| turmeric | 4.8 | immersed in syrup | 38.8 | 53.8 | 79° |
| water | 288 | immersed in oil | 40.6 | 59.2 | 76° |

Example 2

Red Cabbage Coloring Encapsulated in a Soy Protein Isolate

A fine powder of red cabbage color encapsulated in a soy protein isolate matrix was produced (see Table 3). The red cabbage color was diluted in the extruder liquid feed, extruded with soy protein isolate, the resulting extrudate was dried and ground. The dry powder, which possesses a tarnished appearance, takes on an appealing intensely dark, predominantly blue color, once wetted in syrup or oil. Observations of the powder suspended in oil and in syrup were made using an optical microscope. The 10× eye piece had a scale which was calibrated using a calibration slide with a 100 micron marking. The appearance of powder particles suspended in oil and in syrup was identical. Particles were irregular, vitreous (translucent) and uniformly stained. A vast majority of particles measured about 25 microns. The smallest particles measured 5 to 10 microns while very few particles were around 50 microns. The amount of anthocyanin released from the encapsulation matrix in syrup after 15 minutes immersion at room temperature was 40% of the total amount of encapsulated anthocyanin. This composition is suitable for use as a predominantly blue coloring in low moisture and/or non-polar products.

Example 3

Hue Alteration of Red Cabbage Coloring Encapsulated in a Soy Protein Isolate by Calcium Chloride A similar experiment to that shown in Example 2 (see Table 3) was performed, except that calcium chloride was added to the extruder liquid feed in order to alter the color of the extrudate. The resulting powder once wetted in syrup or oil takes on an appealing intensely dark predominantly purple color. The amount of anthocyanin released from the encapsulation matrix in syrup after 15 minutes immersion at room temperature was 15% of the total amount of encapsulated anthocyanin.

Thus, calcium chloride contributes to retaining anthocyanins inside the encapsulation matrix and to altering the color to a more purple shade. This composition is suitable for use as a predominantly purple coloring in low moisture and/or non-polar products.

Example 4

Hue Alteration of Red Cabbage Coloring Encapsulated in a Soy Protein Isolate by Tannic Acid A similar experiment to that shown in Example 2 (see Table 3) was performed, except that tannic acid was added to the extruder liquid feed. The resulting powder once wetted in syrup or oil takes on an appealing dark predominantly mauve color. The amount of anthocyanin released from the encapsulation matrix in syrup after 15 minutes immersion at room temperature was 43% of the total amount of encapsulated anthocyanin.

Thus, tannic acid does not help in retaining anthocyanins inside the encapsulation matrix but shifts the color to a redder hue. This composition is suitable for use as a predominantly mauve coloring in low moisture and/or non-polar products.

Example 5

Beet Red Encapsulated in a Soy Protein Isolate

A fine powder of beet red encapsulated in a soy protein isolate matrix was produced (see Table 3). Beet red and ascorbic acid were dissolved in the extruder liquid feed. The resulting powder once wetted in syrup or oil takes on an appealing moderately dark predominantly purplish-red color. Ascorbic acid serves as a stabilizer of beet red. The amount of betanin released from the encapsulation matrix in syrup after 15 minutes immersion at room temperature was 46% of the total amount of encapsulated betanin. This composition is suitable for use as a predominantly purplish red coloring in low moisture and/or non-polar products.

Example 6

Beet Red and Turmeric Mixture Encapsulated in a Soy Protein Isolate

A similar experiment to that shown in Example 5 (see Table 3) was performed, except that turmeric was also added to the extruder liquid feed by dispersion with a commercial blender. The resulting powder once wetted in syrup or oil takes on an appealing moderately dark predominantly red color. This composition is suitable for use as a predominantly red coloring in low moisture and/or non-polar products.

Example 7

Norbixin Encapsulated in a Soy Protein Isolate

A fine powder of norbixin encapsulated in a soy protein isolate matrix was produced (see Table 3). Norbixin was diluted in the extruder liquid feed. The resulting powder once wetted in syrup or oil takes on an appealing bright predominantly orange color. The amount of norbixin released from the encapsulation matrix in syrup after 15 minutes immersion at room temperature was 9% of the total amount of encapsulated norbixin. This composition is suitable for use as a predominantly orange coloring in low moisture and/or non-polar products.

Example 8

Saffron Encapsulated in a Soy Protein Isolate

A fine powder of saffron (which contains crocin) coloring encapsulated in a soy protein isolate matrix was produced (see Table 3). Saffron was diluted in the extruder liquid feed. The resulting powder once wetted in syrup or oil takes on an appealing bright predominantly golden-yellow color. The amount of crocin released from the encapsulation matrix in syrup after 15 minutes immersion at room temperature was 37% of the total amount of encapsulated crocin. This composition is suitable for use as a predominantly golden-yellow coloring in low moisture and/or non-polar products.

Example 9

Turmeric Encapsulated in a Soy Protein Isolate

A fine powder of turmeric encapsulated in a soy protein isolate matrix was generated (see Table 3). Turmeric was dispersed in the extruder liquid feed using a commercial blender. The resulting powder once wetted in syrup or oil takes on an appealing bright predominantly yellow color. Turmeric is known to be very light-sensitive. However, there were no differences in colorimetry measurements after 20 days of exposure of the encapsulated turmeric to light. The amount of curcuminoids released from the encapsulation matrix in syrup after 15 minutes immersion at room temperature was 6% of the total amount of encapsulated curcuminoids. This composition is suitable for use as a predominantly yellow coloring in low moisture and/or non-polar products.

TABLE 4

Examples of natural colorings and vitamin encapsulated in rice protein concentrate by extrusion

| Extruder feed composition | | Sample preparation prior to colorimeter readings | Colorimeter readings | | |
|---|---|---|---|---|---|
| Ingredient | (g/min) | | $L^*$ | $C^*$ | H |
| Example 10: | | none | 82.8 | 17.8 | 87° |
| rice protein concentrate | 250 | immersed in syrup | 57.6 | 28.5 | 81° |
| water | 200 | immersed in oil | 48.8 | 29.8 | 79° |
| Example 11: | | | | | |
| rice protein concentrate | 250 | none | 40.2 | 13.3 | 307° |
| red cabbage color | 25 | immersed in syrup | 8.0 | 13.1 | 306° |
| water | 175 | immersed in oil | 3.2 | 6.6 | 301° |
| Example 12: | | | | | |
| rice protein concentrate | 250 | none | 45.4 | 12.5 | 301° |
| red cabbage color | 25 | | | | |
| calcium chloride | 25 | immersed in syrup | 7.0 | 12.7 | 301° |
| water | 150 | immersed in oil | 3.9 | 7.8 | 295° |
| Example 13: | | | | | |
| rice protein concentrate | 250 | none | 46.9 | 29.0 | 354° |
| beet red | 25 | | | | |
| ascorbic acid | 6.25 | immersed in syrup | 13.4 | 31.9 | 4° |
| water | 168.75 | immersed in oil | 8.2 | 25.3 | 9° |
| Example 14: | | | | | |
| rice protein concentrate | 250 | none | 33.6 | 18.4 | 8° |
| carminic acid | 3.7 | Immersed in syrup | 2.9 | 9.5 | 8° |
| water | 196.3 | Immersed in oil | 2.1 | 5.7 | 11° |
| Example 15: | | | | | |
| rice protein concentrate | 247.5 | none | 42.9 | 52.8 | 38° |
| bixin | 2.5 | immersed in syrup | 30.4 | 57.8 | 42° |
| water | 200 | immersed in oil | 29.4 | 51.5 | 39° |
| Example 16: | | | | | |
| rice protein concentrate | 250 | none | 79.5 | 58.1 | 90° |
| turmeric | 5 | immersed in syrup | 53.6 | 68.1 | 83° |
| water | 195 | immersed in oil | 45.1 | 63.5 | 79° |

Example 10

Color Characteristics of an Extruded Rice Protein Concentrate

A rice protein concentrate was extruded without an encapsulate under conditions which enable the formation of a melt while minimizing undesirable Maillard reactions (see Table 4). Darkening due to the extrusion process was much less intense than with the soy protein isolate. In fact, differences in the lightness of the dry powder prior to (Table 2) and after extrusion, i.e., $\Delta L^* = -0.4$, was almost negligible. The same holds for extruded powder after immersion in a syrup or in oil, i.e., $\Delta L^* = -0.9$ and $-7.1$, respectively.

The following examples (11 to 16) demonstrate that the matrix of extruded rice protein concentrate is adequate for the encapsulation of dyes while enabling the expression of colors. In general, after immersion in syrup, dyes are better retained inside the encapsulation matrix of rice protein concentrate than the soy protein isolate matrix.

Example 11

Red Cabbage Coloring Encapsulated in a Rice Protein Concentrate

A fine powder of red cabbage color encapsulated in a rice protein concentrate matrix was created (see Table 4). The red cabbage color was diluted in the extruder liquid feed, extruded with rice protein concentrate, the resulting extrudate was dried and ground. The dry powder which possesses a pastel appearance takes on an appealing intensely dark predominantly purple color once wetted in syrup or oil. The amount of anthocyanin released from the encapsulation matrix in syrup after 15 minutes immersion at room temperature was 31% of the total amount of encapsulated anthocyanin. This composition is suitable for use as a predominantly purple coloring in low moisture and/or non-polar products.

Example 12

Hue Alteration of Red Cabbage Coloring Encapsulated in a Rice Protein Concentrate by Calcium Chloride A similar experiment to that shown in Example 11 was performed, except that calcium chloride was added to the extruder liquid feed (see Table 4). The resulting powder once wetted in syrup or oil takes on an appealing intensely dark color similar to that of Example 11. The amount of anthocyanin released from the encapsulation matrix in syrup after 15 minutes immersion at room temperature was 27% of the total amount of encapsulated anthocyanin. Calcium chloride had less effect on the improvement of dye retention and on color change with the rice protein concentrate matrix than with the soy protein isolate matrix (Example 2). This composition is suitable for use as a purple coloring in low moisture and/or non-polar products.

Example 13

Beet Red Encapsulated in a Rice Protein Concentrate

A fine powder of beet red encapsulated in a rice protein concentrate matrix was created (see Table 4). Beet red and ascorbic acid were diluted in the extruder liquid feed. The resulting powder once wetted in syrup or oil takes on an appealing moderately dark predominantly purplish-red color. Ascorbic acid serves as a stabilizer of beet red. The amount of betanin released from the rice protein matrix in syrup after 15 minutes immersion at room temperature was 27% of the total amount of betanin. This composition is suitable for use as a predominantly purplish-red coloring in low moisture and/or non-polar products.

Example 14

Carminic Acid Encapsulated in a Rice Protein Concentrate

A fine powder of carminic acid encapsulated in a rice protein concentrate matrix was generated (see Table 4). Carminic acid was diluted in the extruder liquid feed. The resulting powder once wetted in syrup or oil takes on an appealing moderately dark predominantly brownish-red color. The amount of carminic acid released from the encapsulation matrix in syrup after 15 minutes immersion at room temperature was 23% of the total amount of carminic acid. This composition is suitable for use as a brownish-red coloring in low moisture and/or non-polar products.

Example 15

Bixin Encapsulated in a Rice Protein Concentrate

A fine powder of bixin encapsulated in a rice protein concentrate matrix was produced (see Table 4). Bixin was blended with the rice protein concentrate and introduced into the extruder through the solids feed port. The resulting powder once wetted in syrup or oil takes on an appealing bright predominantly orange color. Bixin, which is insoluble in water at neutral pH, was encapsulated in a rice protein concentrate without having to use an alkali or an emulsifier. No bixin was released from the encapsulation matrix in syrup even after an extended period (several days). This composition is suitable for use as a predominantly orange coloring in low moisture and/or non-polar products. This example also demonstrates that bixin can be used in color blends wherein pH sensitive colorings are used, e.g., anthocyanins, since no pH-altering agent is used in the manufacturing process.

Example 16

Turmeric Encapsulated in a Rice Protein Concentrate

A fine powder of turmeric encapsulated in a rice protein concentrate matrix was created (see Table 4). Turmeric was dispersed in the extruder liquid feed using a commercial blender. The resulting powder once wetted in syrup or oil takes on an appealing bright predominantly yellow color. No turmeric was released from the encapsulation matrix in syrup even after an extended period (several days). This composition is suitable for use as a predominantly yellow coloring in low moisture and/or non-polar products.

Example 17

Tartrazine Encapsulation in a Rice Protein Concentrate

An artificial dye, namely tartrazine, was dissolved in the extruder liquid feed and encapsulated in a rice concentrate at a concentration of 0.1% based on the weight of the dry rice protein concentrate. The colorimetry measurements of the dry yellow powder were: $L^*=80.6$, $C^*=43.6$ and $h=89°$. In water, tartrazine was totally retained inside the encapsulation matrix. No tartrazine was released from the encapsulation matrix in syrup. This composition is suitable for use as a predominantly yellow coloring in low moisture and/or non-polar products.

Encapsulated dyes from Examples 2 to 9 and 11 to 17, were not released from their respective encapsulation matrix when submerged in mineral oil.

Example 18

Usefulness of Encapsulated Dyes for Candy Coatings

The usefulness of encapsulated dyes for candy coatings is presented in examples 18 to 21. A dispersion media similar to those used in candy panning operations, was made by mixing together sucrose, gum acacia and water in a proportion of 60:10:30 by weight and heating to 60° C. Encapsulated dye and the dispersion media were mixed together in a proportion of 5:20 by weight, spread out in plastic Petri dish and dried to form an opaque colored layer similar to that of candy coatings.

A dark predominantly blue layer was obtained from the encapsulated dye of Example 2 (see table 3). Colorimetry measurements were: $L^*=17.2$, $C^*=7.4$ and $h=270°$.

Example 19

An opaque colored layer was obtained by mixing together the encapsulated dye of Example 11, sucrose and gum acacia as described in Example 18. A dark predominantly purple layer was obtained from the encapsulated dye of Example 11. Colorimetry measurements were: L*=24.9, C*=8.3 and h=307°.

Example 20

An opaque colored layer was obtained by mixing together the encapsulated dye of Example 12, sucrose and gum acacia as described in Example 18. A dark predominantly red layer was obtained from the encapsulated dye of Example 12. Colorimetry measurements were: L*=21.2, C*=19.9 and h=2°.

Example 21

An opaque colored layer was obtained by mixing together the encapsulated dye of Example 15, sucrose and gum acacia as described in Example 18. A dark predominantly yellow layer was obtained from the encapsulated dye of Example 15. Colorimetry measurements were: L*=59.7, C*=51.8 and h=82°.

Example 22

Use of Non Polar Coatings

A demonstration of the use of a non-polar coating to water-proof encapsulated dyes is provided herein. The coating was a mixture of (by weight of coating) 2.01% zein, 11.55% canola oil, 82.48% denatured ethanol, 0.66% calcium chloride and 3.30% Durlac 100 W emulsifier. The coating mixture and encapsulated dye of Example 2 were mixed together in a proportion of 3:1 by weight respectively and the denatured ethanol was evaporated. The amount of red cabbage color released from the coated encapsulated dye in syrup after 15 minutes immersion at room temperature was 4% of the total amount of red cabbage color. Therefore the non-polar coating substantially improved impermeability of the encapsulated dye.

Example 23

Encapsulation of a High Concentration of Dye

In some instances it might be desirable to use an encapsulated dye with a higher dye concentration than those of previous Examples to produce thinner color coats with a high color intensity on candies or in other applications. There could also be some economic benefits since the manufacturing of encapsulated dyes with a high dye concentration would not entail significantly different manufacturing costs (without raw materials) than those of an encapsulated dye at a lower dye concentration. This would hold true if it could be demonstrated that the encapsulated dyes can be used at a dosage level proportionate to the amount of dye in the encapsulate. This is demonstrated herein.

Turmeric was encapsulated in a rice protein concentrate at two concentrations in a fashion similar to that of example 16. To achieve this turmeric was dispersed in the extruder liquid feed using a commercial blender at two concentrations. The resulting powders had a turmeric concentration of 1.96% and 9.1% by weight based on the dry weight of encapsulated turmeric. The encapsulated dyes are hereafter referred to as "low dye encapsulate" and "high dye encapsulate" respectively. The high dye encapsulate contained 4.64-fold more turmeric color that the low dye encapsulate.

The low dye and high dye encapsulates were ground to a very fine powders, i.e., particle size averaging 9 microns, using a commercial blender and a ceramic ball mill. A portion of dispersion media was made by mixing together 3 g icing sugar, 0.05 g gum acacia, 1.25 g medium invert sugar, 0.3125 g low bloom gelatin and 2.3875 g water and by heating lightly in a microwave oven until clear. A portion of the low dye encapsulate of 1.64 g was blended with 3.86 g of confectionery sugar and dispersed in a portion of dispersion media. A portion of the high dye encapsulate of 0.28 g was blended with 5.22 g of confectionery sugar and dispersed in a portion of dispersion media. Hence the quantity of low dye encapsulate in the dispersion media was about 5.9-fold higher than the quantity of high dye encapsulate in the dispersion media. The solids content of both mixtures was identical.

Two-gram portions of dispersed dye encapsulates were applied onto the surface of square (48 mm×48 mm) white ceramic tiles and spread evenly over the entire surface using a spatula. The color coatings were dried at room temperature in the dark and color measurements were made. Tiles coated with the dispersion media that contained the low dye encapsulate and the high dye encapsulate had similar L* values, i.e., 85.7 and 85.4 respectively and h values, i.e., 91° and 90° respectively. However, the color vividness was higher for the tiles coated with the dispersion media that contained the high dye encapsulate than the low dye encapsulate, i.e., 49.9 and 35.6 respectively.

Therefore, technical advantages relating to the encapsulation of a high concentration of dye compared to a low concentration of dye include a lower application dosage relative to the actual amount of dye and a brighter color.

Example 24

Encapsulated Dye with a Very High Color Value

This example serves as a demonstration of an encapsulated dye with a very high color value. Bixin 100% is a food color with a very high color value i.e., about 310,000 (determined by spectrophotometry at 458 nm after dilution in ethanol). Encapsulated bixin was produced as in example 15, except that bixin was blended with rice protein concentrate in a proportion of 5:95 (w/w). The encapsulated dye thus obtained contained c.a. 15,500 color units of bixin.

Example 25

Encapsulation Process
Materials
  Proteins:
  Soy protein isolate, Pro-Fam 974 (Archer Daniel Midland, Ill., USA), with a protein content of about 90% based on the dry weight of the isolate; Rice protein concentrate, Remypro N80+(Remy Industries, Leuven-Wijgmaal, Belgium), with a protein content of about 80% based on the dry weight of the concentrate.
  Dyes:
  Beet red, Vegetable Juice Color 4015 (Food Ingredient Solutions, New York N.Y., USA), a beet juice concentrate with a minimum betanin content of 1.5%; Bixin, 100% (Food Ingredient Solutions, New York N.Y., USA); Norbixin, AFC WS 4600P (Rhodia, Madison, Wis., USA), an annatto extract dried using potassium carbonate with a norbixin content of 15%; Red cabbage color (Colarome, St. Hubert, QC, Canada), an aqueous concentrate exempt of diluents with a color value attributable to anthocyanins of 1600 (determined by spectrophotometry at 535 nm in pH 3.0 McMaine buffer); Saffron color, Safrante Industrial (Azafran Natural, Malaga, Spain), a saffron extract dried using maltodextrin; Tartrazine, 07799 FD&C Yellow #5, Granular (Sensient, St. Louis Mo., USA); Turmeric powder P8003 (Food Ingredient Solutions, New York N.Y., USA), a curcuma extract dried using gum acacia as the carrier with a curcumin content of 5±0.4%.

Reagents:

Ascorbic acid, fine granulation (Brenntag Canada, Lachine QC, Canada); Calcium chloride 93%, anhydrous (Brenntag Canada, Lachine QC, Canada); Gelatin, low bloom Kosher (VYSE Gelatin Co., Shiller Park Ill., USA); Gum acacia, Arabic gum Type CS (Daminco, Oakville ON, Canada); Denatured alcohol, SDAG-13, anhydrous (Commercial Alcohols, Tiverton ON, Canada), grain ethyl alcohol denatured with 1% ethyl acetate; Durlac 100 W emulsifier (Loders & Croklaan, Channahon Ill., USA); Medium invert sugar (Nealanders Intl., Dorval QC, Canada); Tannic acid (Fleurchem, Middletown N.Y., USA); Zein F4000, regular grade (Freeman Industries, Tuckahoe N.Y., USA).

Methods

Colorimetry Measurements:

Colorimetry measurements were determined using a ColorFlex™ colorimeter (Hunter Associates Laboratory Inc., Reston, Va.) and a quartz sample cup. Calibration was performed using black and white porcelain color standards and performance of the colorimeter was verified by making readings using a green porcelain standard (illuminant D65/10° observer). Direct color measurements of samples were performed by layering a sufficient amount of sample in the sample cup to ensure opacity. Colorimetry measurements of samples were also performed by suspending samples of encapsulated dyes in a liquid media comprised of either a 50% aqueous solution of sucrose (syrup) or mineral oil, pouring the suspension in the sample cup and letting settle to form an opaque layer of wetted sample before making readings.

Melt Extrusion:

Melt extrusion was accomplished utilizing a Baker-Perkin co-rotating twin-screw extruder (model MPF-50) incorporating 9 sections that can be independently electrically-heated and cooled with chilled water. Solids were introduced using a metering screw through an opening located on top of the third section. A metering pump was used to inject liquids through a port located immediately downstream from the solids port. The die was fitted with two 9 mm orifices and was cooled with chilled water (0° C. to 2° C.). For the extrusion of the soy protein isolate, the two parallel screw assemblies were each comprised of (in the direction of the flow): 10.8 cm spacer, 27.9 cm conveying screw, 10.2 cm single-lead screw, 25.4 cm kneading blocks (20 blocks, 30° forward), 10.2 cm single-lead screw, 11.4 cm kneading blocks (9 blocks, 90°) and 20.3 cm single-lead screw. The assembly of extruder elements used with rice protein concentrate was: 10.8 cm spacer, 27.9 cm conveying screw, 10.2 cm single-lead screw, 25.4 cm kneading blocks (20 blocks, 30° forward), 10.2 cm single-lead screw, 11.4 cm kneading blocks (9 blocks, 30° forward), 5.1 cm kneading blocks (4 blocks, 30° reverse) and 15.2 cm single-lead screw. Temperature settings of the third section through the ninth were respectively 30° C., 35° C., 35° C., 35° C., 10° C., 10° C. and 10° C. Cooling of the sections was performed using chilled water (0° C. to 2° C.). Screw speed was 200 RPM. The extrudate was cut using a 4 blade rotating knife operating at about 1,600 RPM. Of course it should be understood that as the general extrusion process is well known in the art, the particular setting described above (e.g., speed of rotating screw and rotating knife, spacer, conveying screw, lead screw, kneading blocs, single lead screw, temperatures settings, etc. . . . ) could be modified in accordance with the desired characteristics of the extrudate. Thus, other melt extrusion parameters as well as other extruder apparatuses may also be used in accordance with the present invention.

Extrudate Drying and Grinding:

Extrudates were dried at room temperature by layering on paper-lined wire racks and circulating air to a moisture content between 5 and 10% by weight. The resulting dried extrudate was ground using a domestic blender and a fine grind mill (Prater, model CLM18) yielding a powder with particles averaging about 20 microns. Fine powders were produced in Examples 1 to 22 inclusively and Example 24.

Alternatively the dried extrudate was ground using a domestic blender and a ceramic ball mill yielding a very fine powder with particles averaging about 9 microns. Very fine powders were produced in Example 23.

Although the present invention has been described hereinabove by way of preferred embodiments thereof, it can be modified, without departing from the spirit and nature of the subject invention as defined in the appended claims.

What is claimed is:

1. A process for extrusion encapsulation, the process comprising:
   (i) providing an agent to be encapsulated and a water-insoluble protein-rich mixture;
   (ii) mixing said agent, said water-insoluble protein-rich mixture, and water in an extruder at high shearing and pressure to raise the temperature, thereby enabling the formation of a melt; and
   (iii) cooling the melt and extruding at low temperature and high moisture sufficient to minimize browning of the water-insoluble protein by the Maillard reaction, thereby encapsulating said agent in a water-insoluble protein-rich matrix.

2. The process of claim 1, further comprising:
   (iv) drying the extruded mixture to a moisture content of between 5 to 10% by weight, based on the total weight of said dried extruded mixture, wherein said dried extruded mixture comprises at least 70% by weight of water insoluble protein, based on the total weight of said matrix.

3. The process of claim 2, further comprising:
   (v) milling or grinding said dried extruded mixture to form a dry particulate extrudate.

4. The process of claim 3, wherein said dried extruded mixture is milled or ground to particles having an average size smaller than 150 microns.

5. The process of claim 1, wherein said water-insoluble protein-rich mixture is a plant-derived water-insoluble protein-rich mixture.

6. The process of claim 5, wherein said water-insoluble plant protein-rich mixture is or comprises a rice protein and/or a soy protein.

7. The process of claim 5, wherein said water-insoluble plant protein-rich mixture is or comprises a rice protein concentrate having a rice protein content above 77% by weight, based on the dry weight of said rice protein concentrate; or wherein said water-insoluble plant protein-rich mixture is or comprises a soy protein isolate having a soy protein content above 87% by weight, based on the dry weight of said soy protein isolate.

8. The process of claim 5, wherein the water-insoluble plant protein-rich mixture is a rice protein concentrate, and wherein said extrusion is performed at a moisture content of 30 to 50% by weight, based on the total weight of said rice protein concentrate and water.

9. The process of claim 5, wherein the water-insoluble plant protein-rich mixture is a soy protein isolate, and wherein said extrusion is performed at a moisture content of 45 to 70% by weight, based on the total weight of said soy protein isolate and water.

10. The process of claim 1, wherein the temperature of the extruder during extruding is set to a temperatures between 10° C. and 35° C.

11. The process of claim 1, wherein said agent to be encapsulated is a labile agent, a heat-sensitive agent, and/or a light-sensitive agent.

12. The process of claim 1, wherein said agent is a coloring agent or a labile coloring agent.

13. The process of claim 2, wherein said agent is a coloring agent or a labile coloring agent.

14. The process of claim 3, wherein said agent is a coloring agent or a labile coloring agent.

15. The process of claim 1, wherein said agent is: a natural dye, a nature-identical dye, an artificial dye, a lake of a natural dye, a synthetic dye, a synthetic lake, or any combination thereof.

16. The process of claim 15, wherein said natural dye is an anthraquinone, a betalain, caramel, a carotenoid, a curcuminoid, a flavin, a flavonoid, a porphyrin, geniposide, sandalwood, sepia, or vegetable black.

17. The process of claim 16, wherein: (a) said flavonoid is obtained from at least one of: red cabbage, sweet potato, red radish, elderberry and grape; (b) said betalain is beet red; (c) said anthraquinone is carminic acid or carmine; (d) said carotenoid is: annatto, apocarotenal, apocarotenal ester, canthaxanthin, beta-carotene, lycopene, lutein, paprika, saffron, bixin, norbixin or crocin; (e) said porphyrin is chlorophyll or chlorophyllin; (f) said curcuminoid is turmeric; and (g) said flavin is riboflavin.

18. The process of claim 1, wherein said water-insoluble protein-rich matrix, once wetted in a clear colorless aqueous solution or in mineral oil, has a lightness value (L*) greater than 40, a color vividness or Chroma (C*) lower than 33 and a hue angle between 70° and 90°, according to the CIE Lch color space developed by the Commission Internationale d'Éclairage.

19. The process of claim 1, wherein the melt in (ii) further comprises:
  (a) an organic acid, an inorganic acid, a calcium salt, or any combination thereof; and/or
  (b) a stabilizer or preservative agent which is: alpha-tocopherol, ascorbic acid, benzoic acid, isoascorbic acid, butylated hydroxyanisole, butylated hydroxytoluene, sodium citrate, sorbic acid, potassium, sodium bisulphate, or any combination thereof.

20. The process of claim 3, further comprising enrobing the dry particulate extrudate in a non-polar coating comprising: waxes, oils, fats, long chain fatty acid, an acacia, gelatin, lecithin, cholesterol, sulfates or sulfonates, gums, zein, an emulsifier, or any mixture thereof.

21. The process of claim 3, wherein said dried extruded mixture is milled or ground to particles having an average size smaller than 50 microns.

22. The process of claim 3, wherein said dried extruded mixture is milled or ground to particles having an average size smaller than 20 microns.

23. The process of claim 3, wherein said dried extruded mixture is milled or ground to particles having an average size smaller than 10 microns.

24. The process of cam 19, wherein the organic acid is tannic acid, ascorbic acid, or a combination thereof.

* * * * *

UNITED STATES PATENT AND TRADEMARK OFFICE
CERTIFICATE OF CORRECTION

PATENT NO. : 10,981,136 B2  
APPLICATION NO. : 15/933852  
DATED : April 20, 2021  
INVENTOR(S) : Huynh et al.

It is certified that error appears in the above-identified patent and that said Letters Patent is hereby corrected as shown below:

In the Claims

In Claim 10, Column 25, Line 7, "a temperatures between" should be --a temperature between--.

In Claim 24, Column 26, Line 31, "of cam 19" should be --of claim 19--.

Signed and Sealed this  
Eighth Day of February, 2022

Drew Hirshfeld  
*Performing the Functions and Duties of the*  
*Under Secretary of Commerce for Intellectual Property and*  
*Director of the United States Patent and Trademark Office*